United States Patent
Merritt et al.

(10) Patent No.: US 7,427,408 B2
(45) Date of Patent: Sep. 23, 2008

(54) QUORUM SENSING AND BIOFILM FORMATION

(75) Inventors: Justin Merritt, Los Angeles, CA (US);
Wenyuan Shi, Los Angeles, CA (US);
Maxwell H. Anderson, Seattle, WA (US)

(73) Assignee: The Regents of the University of California, Oakland, CA (US)

( * ) Notice: Subject to any disclaimer, the term of this patent is extended or adjusted under 35 U.S.C. 154(b) by 1078 days.

(21) Appl. No.: 10/164,446

(22) Filed: Jun. 6, 2002

(65) Prior Publication Data

US 2003/0229000 A1    Dec. 11, 2003

(51) Int. Cl.
*A01N 25/00* (2006.01)
*A61K 35/66* (2006.01)
*A61K 38/00* (2006.01)

(52) U.S. Cl. .................... 424/405; 424/780; 424/50; 514/2

(58) Field of Classification Search .................... 435/29, 435/4, 885; 424/244.1
See application file for complete search history.

(56) References Cited

U.S. PATENT DOCUMENTS

| | | | | |
|---|---|---|---|---|
| 5,874,068 | A * | 2/1999 | Engelman et al. | 424/54 |
| 5,891,422 | A * | 4/1999 | Pan et al. | 424/49 |
| 6,254,856 | B1 * | 7/2001 | Tsuchiya | 424/49 |
| 6,309,835 | B1 * | 10/2001 | Iyer et al. | 435/6 |
| 6,559,176 | B1 * | 5/2003 | Bassler et al. | 514/408 |
| 2003/0171421 | A1 * | 9/2003 | Davies et al. | 514/445 |
| 2003/0228379 | A1 * | 12/2003 | Shi et al. | 424/725 |
| 2003/0229000 | A1 * | 12/2003 | Merritt et al. | 514/1 |
| 2004/0023254 | A1 * | 2/2004 | Fuhrmann et al. | 435/6 |
| 2004/0147595 | A1 * | 7/2004 | Kjelleberg et al. | 514/463 |

FOREIGN PATENT DOCUMENTS

WO    WO 01/85664 A2 *  11/2001

OTHER PUBLICATIONS

Li et al. J. Bacteriol. Feb. 2001. vol. 183, No. 3, pp. 897-908.*
Li et al. Abstracts of the General Meeting of the Am. Soc. Microbiol. May 2001. vol. 101, p. 442, BIOSIS Abstract enclosed.*
Yoshida et al. Abstracts of the General Meeting of the Am. Soc. Microbiol. May 2001. vol. 101, pp. 326-327, BIOSIS Abstract enclosed.*
Yoshida et al. Abstracts of the General Meeting of the Am. Soc. Microbiol. May 2002. vol. 102, p. 161, BIOSIS Abstract enclosed.*
Karen P. Fong, et al., "Intra- and Interspecies Regulation of Gene Expression by *Actinobacillus actinomycetemcomitans* LuxS," Infection and Immunity, vol. 69, No. 12, pp. 7625-7634 (2001).
Clay Fuqua, et al., "Self Perception in Bacteria: Quorum Sensing with Acylated Homoserine Lactones," Current Opinion in Microbiology, pp. 183-189 (1998).

Matthew R. Parsek, et., "Acyl-homoserine Lactone Quorum Sensing in Gram-negative Bacteria: A Signaling Mechanism Involved in Associations with Higher Organisms," Colloquium, vol. 97, No. 16, pp. 8789-8793 (2000).
Cuong Vuong, et al., "Impact of the *agr* Quorum-Sensing System on Adherence to Polystyrene in *Staphylococcus aureus*," The Journal of Infectious Diseases, vol. 182, pp. 1688-1693 (2000).
Xin Chen, et al., "Structural Identification of a Bacterial Quorum-Sensing Signal Containing Boron," Nature, vol. 415, pp. 545-549 (2002).
Birgit Huber, et al., "The Cep Quorum-Sensing System of *Burkholderia cepacia* H111 Controls Biofilm Formation and Swarming Motility," Microbiology, vol. 147, pp. 2517-2528 (2001).
P. Stoodley, et al., "Biofilms as Complex Differentiated Communities," Ann. Rev. Microbiol., vol. 56, pp. 187-209 (2002).
Jean Barbeau, et al., "Biofilms, Infectious Agents, and Dental Unit Waterlines: A Review," Can. J. Microbiol., vol. 44, pp. 1019-1028 (1998).
David Stickler, "Biofilms," Current Opinion in Microbiology, vol. 2, pp. 270-275 (1999).
David G. Davies, et al., "The Involvement of Cell-to-Cell Signals in the Development of a Bacterial Biofilm," Science, vol. 280, pp. 295-298 (1998).
Vanessa Sperandio, et al., "Quorum Sensing Controls Expression of the Type III Secretion Gene Transcription and Protein Secretion in Enterohemorrhagic and Enteroptahogenic *Escherichia coli*," PNAS, vol. 96, No. 26, pp. 15196-15201 (1999).
Michael G. Surette, et al., "Quorum Sensing in *Escherichia coli* and *Salmonella typhimurium*," Proc. Natl. Acad. Sci. USA, vol. 95, pp. 7046-7050 (1998).
Zezhang T. Wen, et al., "Functional Genomics Approach to Identifying Genes Required to Biofilm Development by *Streptococcus mutans*," Applied and Environmental Microbiology, vol. 68, No. 3, pp. 1196-1203 (2002).
Paul E. Kolenbrander, et al., "Intergeneric Coaggregation of Oral *Treponema* spp. With *Fusobacterium* spp. And Intrageneric Coaggregation among *Fusobacterium* spp.," Infection and Immunity, vol. 63, No. 12, pp. 4584-4588 (1995).
Karsten R. O. Hazlett, et al., "Inactivation of the *gbpA* Gene of *Streptococcus mutans* Alters Structural and Functional Aspects of Plaque Biofilm which are Compensated by Recombination of the *gtfB* and *gtfC* Genes," Infection and Immunity, vol. 67, No. 8, pp. 3909-3914 (1999).
Renata O. Mattos-Graner, et al., "Cloning of the *Streptococcus mutans* Gene Encoding Glucan Binding Protein B and Analysis of Genetic Diversity and Protein Production in Clinical Isolates," Infection and Immunity, vol. 69, No. 11, pp. 6931-6941 (2001).

(Continued)

*Primary Examiner*—Christopher R. Tate
(74) *Attorney, Agent, or Firm*—Michael J. Wise; Perkins Coie LLP

(57) ABSTRACT

The present invention is based on the discovery that interspecies quorum sensing is related to biofilm formation. The present invention provides methods useful for treating or preventing biofilm formation and microbial infections associated with biofilm formation by using an agent that either increases LuxS-dependent pathway or interspecies quorum sensing signal. The present invention also provides compositions containing an anti-microbial agent and an agent that either increases LuxS-dependent pathway or interspecies quorum sensing signal.

27 Claims, 6 Drawing Sheets

OTHER PUBLICATIONS

Leslie A. Pratt, et al., "Genetic Analyses of Bacterial Biofilm Formation," Current Opinion in Microbiology, vol. 2, pp. 598-603 (1999).

Gary M. Dunny, et al., "Cell-Cell Communication in Gram-Positive Bacteria," Annu. Rev. Microbiol., vol. 51, pp. 527-564 (1997).

Elizabeth A. Joyce, et al., "Evidence for a Signaling System in *Helicobacter pylori*: Detection of a *luxS*-Encoded Autoinducer," Journal of Bacteriology, vol. 182, No. 13, pp. 3638-3643 (2000).

Mark H. Forsyth, et al., "Intercellular Communication in *Helicobacter pylori*: *luxS* is Essential for the Production of an Extracellular Signaling Molecule," Infection and Immunity, vol. 68, No. 6, pp. 3193-3199 (2000).

S. N. Ruzheinikov, et al., The 1.2 Å Structure of a Novel Quorum-Sensing Protein, *Bacillus subtilis* LuxS, J. Mol. Biol., vol. 313, pp. 111-122 (2001).

Stephan Schauder, et al., The LuxS Family of Bacterial Autoinducers: Biosynthesis of a Novel Quorum-Sensing Signal Molecule, Molecular Biology, vol. 41, Issue 2, pp. 463-476 (2001).

Michael G. Surette, et al., "Quorum Sensing in *Escherichia coli*, *Salmonella typhimuruium* and *Vibrio harveyi*: A New Family of Genes Responsible for Autoinducer Production," Proc. Natl. Acad. Sci. USA, vol. 96, pp. 1639-1644 (1999).

Mary Ellen Davey, et al., "Microbial Biofilms: form Ecology to Molecular Genetics," Microbiology and Molecular Biology Reviews, pp. 847-867 (2000).

Ping Chen, et al., "The Specific Genes for Lantibiotic Mutacin II Biosynthesis in *Streptococcus mutans* T8 Are Clustered and Can Be Transferred En Bloc," Applied and Environmental Microbiology, pp. 1356-1360 (1999).

Fengxia Qi, et al., "Purification of Mutacin III from Group III *Streptococcus mutans* UA787 and Genetic Analyses of Mutacin III Biosynthesis Genes," Applied and Environmental Microbiology, vol. 65, No. 9, pp. 3880-3887 (1999).

Fengxia Qi, et al., "The Group I Strain of *Streptococcus mutans*, UA140, Produces Both the Lantibiotic Mutacin I and a Nonlantibiotic Bacteriocin, Mutacin IV," Applied and Environmental Microbiology, vol. 67, No. 1, pp. 15-21 (2001).

Paul E. Kolenbrander, "Oral Microbial Communities: Biofilms, Interactions, and Genetic Systems," Annu. Rev. Microbiol., vol. 54, pp. 413-437 (2000).

Jorge Frias, et al., "Periodontal Pathogens Produce Quorum Sensing Signal Molecules," Infection and Immunity, vol. 69, No. 5, pp. 3431-3434 (2001).

Whasun O. Chung, et al., "Signaling System in *Porphyromonas gingivalis* Based on a LuxS Protein," Journal of Bacteriology, pp. 3903-3909 (2001).

Bonnie L. Bassler, "How Bacteria Talk to Each Other: Regulation of Gene Expression by Quorum Sensing," Current Opinion in Microbiology, vol. 2, pp. 582-587 (1999).

William A. Day, Jr., et al., "*Shigella flexneri* LuxS Quorum-Sensing System Modulates *virB* Expression but Is Not Essential for Virulence," Infection and Immunity, vol. 69, No. 1, pp. 15-23 (2001).

C.Y. Loo, et al., "*Streptococcus gordonii* Biofilm Formation: Identification of Genes that Code for Biofilm Phenotypes," Journal of Bacteriology, vol. 182, No. 5, pp. 1374-1382 (2000).

William R. Lyon, et al., "Mutation of *luxS* Affects Growth and Virulence Factor Expression in *Streptococcus pyogenes*," Molecular Microbiology, vol. 42, Issue 1, pp. 145-157 (2001).

W. Shi, et al., "Rapid and Quantitative Detection of *Streptococcus mutans* with Species-Specific Monoclonal Antibodies," Hybridoma, vol. 17, No. 4, pp. 365-371 (1998).

Li et al., "A quorum-sensing system essential for induction of genetic competence in *Streptococcus mutans* is involved in biofilm formation," Abstracts of the General Meeting of the American Society for Microbiology (2001) 101:442.

* cited by examiner

```
            10        20        30        40        50        60
1   MP---LLDSFTVDHTRMNAPAVRVAKTMQTPKGDTITVFDLRFTAPNKDILSEKGIHTLE    57
2   MTKEVTVESFELDHIAVKAPYVRLISEEFGPKGDLITNFDIRLVQPNEDSIPTAGLHTIE    60
3   MP---LLDSFTVDHTRMEAPAVRVAKTMNTPHGDAITVFDLRFCVPNKEVMPERGIHTLE    57
4   MTKEVIVESFELDHTIVKAPYVRLISEEFGPKGDRITNFDVRLVQPNQNSIETAGLHTIE    60
5   MP---SVESFELDHNAVVAPYVRHCGVHKVGTDGVVNKFDIRFCQPNKQAMKPDTIHTLE    57

70        80        90       100       110       120
1   HLYAGFMRNHLNG-DSVEIIDISPMGCRTGFYMSLIGTPSEQQVADAWIAAMEDVLKVEN   116
2   HLLAKLIRQRIDG-----MIDCSPFGCRTGFHLIMWGKHTTTQIATVIKASLEEIANTIS   115
3   HLFAGFMRNHLNG-NGVEIIDISPMGCRTGFYMSLIGTPDEQRVADVWKAAMEDVLKVQD   116
4   HLLAKLIRQRIDG-----MIDCSPFGCRTGFHLIMWGKHSSTDIAKVIKSSLEEIATGIT   115
5   HLLAFTIRSHAEKYDHFDIIDISPMGXQTGYYLVVSGETTSAEIVDLLEDTMKEAVEI--   115

130       140       150       160       170
1   QNKIPELNEYQCGTAAMHSLDEAKQIAKNILEVGVAVNKNDELALPESMLRELRID      172
2   WKDVPGTTIESCGNYKDHSLFSAKEWAKLILKQGI----SDD---PFERHLV----      160
3   QNQIPELNVYQCGTYQMHSLQEAQDIARSILERDVRINSNEEALALPKEKLQELH--     170
4   WEDVPGTTLESCGNYKDHSLFAAKEWAQLIIDQGI----SDD---PFSRHVI----      160
5   -TEIPAANEKQCGQAKLHDLEGAKRLMRFWLSQD-----KEE---LLKVFG-----      157
```

FIGURE 1

SEQUENCE LISTING

<160> NUMBER OF SEQ ID NOS: 17

<210> SEQ ID NO 1
<211> LENGTH: 160
<212> TYPE: PRT
<213> ORGANISM: Streptococcus mutans

<400> SEQUENCE: 1

Met Thr Lys Glu Val Thr Val Glu Ser Phe Glu Leu Asp His Ile Ala
1               5                   10                  15

Val Lys Ala Pro Tyr Val Arg Leu Ile Ser Glu Glu Phe Gly Pro Lys
            20                  25                  30

Gly Asp Leu Ile Thr Asn Phe Asp Ile Arg Leu Val Gln Pro Asn Glu
            35                  40                  45

Asp Ser Ile Pro Thr Ala Gly Leu His Thr Ile Glu His Leu Leu Ala
            50                  55                  60

Lys Leu Ile Arg Gln Arg Ile Asp Gly Met Ile Asp Cys Ser Pro Phe
65                  70                  75                  80

Gly Cys Arg Thr Gly Phe His Leu Ile Met Trp Gly Lys His Thr Thr
            85                  90                  95

Thr Gln Ile Ala Thr Val Ile Lys Ala Ser Leu Glu Glu Ile Ala Asn
            100                 105                 110

Thr Ile Ser Trp Lys Asp Val Pro Gly Thr Thr Ile Glu Ser Cys Gly
            115                 120                 125

Asn Tyr Lys Asp His Ser Leu Phe Ser Ala Lys Glu Trp Ala Lys Leu
            130                 135                 140

Ile Leu Lys Gln Gly Ile Ser Asp Asp Pro Phe Glu Arg His Leu Val
145                 150                 155                 160

<210> SEQ ID NO 2
<211> LENGTH: 172
<212> TYPE: PRT
<213> ORGANISM: Vibrio harveyi

<400> SEQUENCE: 2

Met Pro Leu Leu Asp Ser Phe Thr Val Asp His Thr Arg Met Asn Ala
1                   5                   10                  15

Pro Ala Val Arg Val Ala Lys Thr Met Gln Thr Pro Lys Gly Asp Thr
            20                  25                  30

Ile Thr Val Phe Asp Leu Arg Phe Thr Ala Pro Asn Lys Asp Ile Leu
            35                  40                  45

Ser Glu Lys Gly Ile His Thr Leu Glu His Leu Tyr Ala Gly Phe Met
            50                  55                  60

Arg Asn His Leu Asn Gly Asp Ser Val Glu Ile Asp Ile Ser Pro
65                  70                  75                  80

Met Gly Cys Arg Thr Gly Phe Tyr Met Ser Leu Ile Gly Thr Pro Ser
            85                  90                  95

Glu Gln Gln Val Ala Asp Ala Trp Ile Ala Ala Met Glu Asp Val Leu
            100                 105                 110

Lys Val Glu Asn Gln Asn Lys Ile Pro Glu Leu Asn Glu Tyr Gln Cys
            115                 120                 125

Gly Thr Ala Ala Met His Ser Leu Asp Glu Ala Lys Gln Ile Ala Lys
            130                 135                 140

Asn Ile Leu Glu Val Gly Val Ala Val Asn Lys Asn Asp Glu Leu Ala
145                 150                 155                 160

Leu Pro Glu Ser Met Leu Arg Glu Leu Arg Ile Asp
            165                 170

<210> SEQ ID NO 3
<211> LENGTH: 170
<212> TYPE: PRT
<213> ORGANISM: Escherichia coli

<400> SEQUENCE: 3

Met Pro Leu Leu Asp Ser Phe Thr Val Asp His Thr Arg Met Glu Ala
1                   5                   10                  15

Pro Ala Val Arg Val Ala Lys Thr Met Asn Thr Pro His Gly Asp Ala
            20                  25                  30

Ile Thr Val Phe Asp Leu Arg Phe Cys Val Pro Asn Lys Glu Val Met
        35                  40                  45

Pro Glu Arg Gly Ile His Thr Leu Glu His Leu Phe Ala Gly Phe Met
    50                  55                  60

Arg Asn His Leu Asn Gly Asn Gly Val Glu Ile Ile Asp Ile Ser Pro
65                  70                  75                  80

Met Gly Cys Arg Thr Gly Phe Tyr Met Ser Leu Ile Gly Thr Pro Asp
                85                  90                  95

Glu Gln Arg Val Ala Asp Val Trp Lys Ala Ala Met Glu Asp Val Leu
            100                 105                 110

Lys Val Gln Asp Gln Asn Gln Ile Pro Glu Leu Asn Val Tyr Gln Cys
        115                 120                 125

Gly Thr Tyr Gln Met His Ser Leu Gln Glu Ala Gln Asp Ile Ala Arg
    130                 135                 140

Ser Ile Leu Glu Arg Asp Val Arg Ile Asn Ser Asn Glu Glu Leu Ala
145                 150                 155                 160

Leu Pro Lys Glu Lys Leu Gln Glu Leu His
                165                 170

<210> SEQ ID NO 4
<211> LENGTH: 160
<212> TYPE: PRT
<213> ORGANISM: Streptococcus pyogenes

<400> SEQUENCE: 4

Met Thr Lys Glu Val Ile Val Glu Ser Phe Glu Leu Asp His Thr Ile
1               5                   10                  15

Val Lys Ala Pro Tyr Val Arg Leu Ile Ser Glu Glu Phe Gly Pro Lys
            20                  25                  30

Gly Asp Arg Ile Thr Asn Phe Asp Val Arg Leu Val Gln Pro Asn Gln
        35                  40                  45

Asn Ser Ile Glu Thr Ala Gly Leu His Thr Ile Glu His Leu Leu Ala
    50                  55                  60

Lys Leu Ile Arg Gln Arg Ile Asp Gly Met Ile Asp Cys Ser Pro Phe
65                  70                  75                  80

Gly Cys Arg Thr Gly Phe His Leu Ile Met Trp Gly Lys His Ser Ser
                85                  90                  95

Thr Asp Ile Ala Lys Val Ile Lys Ser Ser Leu Glu Glu Ile Ala Thr
            100                 105                 110

Gly Ile Thr Trp Glu Asp Val Pro Gly Thr Thr Leu Glu Ser Cys Gly
        115                 120                 125

Asn Tyr Lys Asp His Ser Leu Phe Ala Ala Lys Glu Trp Ala Gln Leu
    130                 135                 140

Ile Ile Asp Gln Gly Ile Ser Asp Asp Pro Phe Ser Arg His Val Ile
145                 150                 155                 160

<210> SEQ ID NO 5
<211> LENGTH: 157
<212> TYPE: PRT
<213> ORGANISM: Bacillus subtilis
<220> FEATURE:
<221> NAME/KEY: MISC_FEATURE
<222> LOCATION: (84)..(84)
<223> OTHER INFORMATION: Xaa is any amino acid

```
<400> SEQUENCE: 5

Met Pro Ser Val Glu Ser Phe Glu Leu Asp His Asn Ala Val Val Ala
1               5                   10                  15

Pro Tyr Val Arg His Cys Gly Val His Lys Val Gly Thr Asp Gly Val
            20                  25                  30

Val Asn Lys Phe Asp Ile Arg Phe Cys Gln Pro Asn Lys Gln Ala Met
        35                  40                  45

Lys Pro Asp Thr Ile His Thr Leu Glu His Leu Leu Ala Phe Thr Ile
    50                  55                  60

Arg Ser His Ala Glu Lys Tyr Asp His Phe Asp Ile Ile Asp Ile Ser
65                  70                  75                  80

Pro Met Gly Xaa Gln Thr Gly Tyr Tyr Leu Val Val Ser Gly Glu Thr
                85                  90                  95

Thr Ser Ala Glu Ile Val Asp Leu Leu Glu Asp Thr Met Lys Glu Ala
            100                 105                 110

Val Glu Ile Thr Glu Ile Pro Ala Ala Asn Glu Lys Gln Cys Gly Gln
        115                 120                 125

Ala Lys Leu His Asp Leu Glu Gly Ala Lys Arg Leu Met Arg Phe Trp
    130                 135                 140

Leu Ser Gln Asp Lys Glu Glu Leu Leu Lys Val Phe Gly
145                 150                 155

<210> SEQ ID NO 6
<211> LENGTH: 18
<212> TYPE: DNA
<213> ORGANISM: Artificial sequence
<220> FEATURE:
<223> OTHER INFORMATION: PCR primer

<400> SEQUENCE: 6
gatgctgcac gctctgtc                                                 18

<210> SEQ ID NO 7
<211> LENGTH: 19
<212> TYPE: DNA
<213> ORGANISM: Artificial sequence
<220> FEATURE:
<223> OTHER INFORMATION: PCR primer

<400> SEQUENCE: 7
gcagttaggg tatccatcc                                                19

<210> SEQ ID NO 8
<211> LENGTH: 28
<212> TYPE: DNA
<213> ORGANISM: Artificial sequence
<220> FEATURE:
<223> OTHER INFORMATION: Amplification primer

<400> SEQUENCE: 8
gcggatcctc aagctctcaa gcgttcgg                                      28

<210> SEQ ID NO 9
<211> LENGTH: 28
<212> TYPE: DNA
<213> ORGANISM: Artificial sequence
<220> FEATURE:
<223> OTHER INFORMATION: Amplification primer

<400> SEQUENCE: 9
cgagatctat aagacggaca taaggggc                                      28
```

```
<210> SEQ ID NO 10
<211> LENGTH: 29
<212> TYPE: DNA
<213> ORGANISM: Artificial sequence
<220> FEATURE:
<223> OTHER INFORMATION: Amplification primer

<400> SEQUENCE: 10
gcctcgagca gatgatcctt ttgagcgtc                              29

<210> SEQ ID NO 11
<211> LENGTH: 28
<212> TYPE: DNA
<213> ORGANISM: Artificial sequence
<220> FEATURE:
<223> OTHER INFORMATION: Amplification primer

<400> SEQUENCE: 11
cgtctagacg gatgcaaaga gaacgaag                               28

<210> SEQ ID NO 12
<211> LENGTH: 20
<212> TYPE: DNA
<213> ORGANISM: Artificial sequence
<220> FEATURE:
<223> OTHER INFORMATION: PCR primer

<400> SEQUENCE: 12
aagagtttgg acctaaaggc                                        20

<210> SEQ ID NO 13
<211> LENGTH: 20
<212> TYPE: DNA
<213> ORGANISM: Artificial sequence
<220> FEATURE:
<223> OTHER INFORMATION: PCR primer

<400> SEQUENCE: 13
cccacaggac tcaatagttg                                        20

<210> SEQ ID NO 14
<211> LENGTH: 21
<212> TYPE: DNA
<213> ORGANISM: Artificial sequence
<220> FEATURE:
<223> OTHER INFORMATION: PCR primer

<400> SEQUENCE: 14
ctcgacgaat aggatcaaag c                                      21

<210> SEQ ID NO 15
<211> LENGTH: 21
<212> TYPE: DNA
<213> ORGANISM: Artificial sequence
<220> FEATURE:
<223> OTHER INFORMATION: PCR primer

<400> SEQUENCE: 15
gagccatcac acagcaaaaa c                                      21

<210> SEQ ID NO 16
<211> LENGTH: 22
<212> TYPE: DNA
<213> ORGANISM: Artificial sequence
<220> FEATURE:
```

```
<223> OTHER INFORMATION: PCR primer

<400> SEQUENCE: 16
agtgtgttga tagtgcagta tc                                              22

<210> SEQ ID NO 17
<211> LENGTH: 20
<212> TYPE: DNA
<213> ORGANISM: Artificial sequence
<220> FEATURE:
<223> OTHER INFORMATION: PCR primer

<400> SEQUENCE: 17
gaagctgtca gtagtatacc                                                 20
```

QUORUM SENSING AND BIOFILM FORMATION

FIELD OF THE INVENTION

This invention relates generally to the field of biofilm formation, especially bacterial biofilm formation associated with interspecies quorum sensing.

BACKGROUND OF THE INVENTION

A bacterial biofilm is a community of bacteria (either single or multiple bacterial species) that adhere to a solid surface (Davey, M. E., et al., *Microbiol Mol Biol Rev*, 64:847–67 (2000)). In recent years, biofilms have received much attention due to their impact on industry and medicine. Biofilms are responsible for a plethora of problems ranging from biofouling of pipelines to facilitating tissue damage in Cystic Fibrosis patients (Barbeau, J., et al., *Can J Microbiol*, 44:1019–28 (1998)); Stickler, D., *Curr Opin Microbiol*, 2:270–5 (1999)); and Wen, Z. T., et al., *Appl Environ Microbiol*, 68:1196–203 (2002)).

Studies have clearly shown that a bacterial biofilm is not a result of random accretions of bacterial cells; rather, it is the net result of a community of bacteria cooperating to form well-differentiated structures (Costerton, J. W., et al., *Annu Rev Microbial*, 64:847–67 (2000)). The production of biofilm is dependent on the progression through several steps, from initial attachment to full maturity as a stable ecologic system (Pratt, L., et al., *Curr Opin Microbiol*, 2:598–603 (1999)). Given the tremendous metabolic and physiological changes that are required for the switch from planktonic to biofilm growth, it would seem reasonable that there exist some gene regulators responsible for facilitating this process. Indeed various gene regulation systems have been found to be involved in bacterial biofilm formation (Davies, D. G., et al., *Science*, 280:295–8 (1998)).

Quorum sensing is a mechanism for bacteria to change gene expression at very specific cell densities. To date, there are two types of recognized quorum sensing systems in bacteria. The first, known as intraspecies quorum systems, are species specific. In Gram-negative bacteria, intraspecies quorum signals are composed of an acyl-homoserine lactone backbone with species specific substitutions, while Gram-positive bacteria use various peptides as their signals (Dunny G. M., et al., *Annu Rev Microbiol*, 51:527–64 (1997); Fuqua, C., et al., *Curr Opin Microbiol*, 1:183–9 (1998); and Parsek, M. R., et al., *Proc Natl Acad Sci USA*, 97:8789–93 (2000)).

Recently, a second quorum sensing system was characterized in *Vibrio harveyi*. This system is referred to as the interspecies quorum system and is believed to operate as a universal quorum system for many bacteria possessing the characteristic luxS gene (Bassler, B. L., *Curr Opin Microbiol*, 2:582–7 (1999); Schauder, S., et al., *Mol Microbiol*, 41:463–76 (2001); and Surette, M. G., et al., *Proc Natl Acad Sci USA*, 96:1639–44 (1999)). The luxS gene is highly conserved among many species of Gram-negative and Gram-positive bacteria and is thought to be responsible for synthesizing a universally recognized quorum signal referred to as autoinducer-2 (AI-2) (Surette, M. G., et al., *Proc Natl Acad Sci USA*, 96:1639–44 (1999)). The chemical structure of the actual signal is still under investigation, however, crystallographic studies of the AI-2 receptor in *Vibrio harveyi* seem to suggest that AI-2 is a furanosyl borate diester formed from the metabolite 4,5-dihydroxy-2,3-pentadione (Chen, X., et al., *Nature*, 415:545–9 (2002); Ruzheinikov, S. N., et al., *J Mol Biol*, 313:111–22 (2001); and Schauder, S., et al., *Mol Microbiol*, 41:463–76 (2001)).

One feature regarding quorum sensing that has been extensively studied, is the link between intraspecies quorum sensing and biofilm related gene expression. There are several well-characterized examples for the involvement of intraspecies quorum sensing and biofilm formation. For example, lasI of *Pseudomonas aeruginosa* directs the synthesis of an acyl-homoserine lactone signal molecule used for *P. aeruginosa* intraspecies quorum signaling (Davies, D. G., et al. *Science*, 280:295–8 (1998)). Mutants in this gene were unable to produce biofilms that progressed beyond the very early stages of biofilm development (Davies, D. G., et al. *Science*, 280:295–8 (1998)). However, exogenous addition of the appropriate signal complemented the defect (Davies, D. G., et al. *Science*, 280:295–8 (1998)).

A similar result was also obtained due to inactivation of the cep intraspecies quorum sensing system of *Burkholderia cepacia* (Huber, B., et al., *Microbiology*, 147:2517–28 (2001)). Furthermore, a transposon mutagenesis study of the oral pathogen *Streptococcus gordonii* had detected a severe biofilm deficiency due to disruption of the two component system required for its intraspecies quorum sensing system (Loo, C. Y., et al., *J Bacteriol*, 182:1374–82 (2000)).

In *Staphylococcus aureus*, intraspecies quorum signaling has been implicated as a negative regulator of biofilm formation (Vuong, C., et al., *J Infect Dis*, 182:1688–93 (2000)). LuxS-dependent AI-2 signals have also been detected in a variety of bacterial species and found to be involved in various cellular processes in a cell density dependent manner (Day, W. A., Jr., et al., *Infect Immun*, 69:15–23 (2001); Forsyth, M. H., et al., *Infect Immun*, 68:3193–9 (2000); Frias, J., et al., *Infect Immun*, 69:3431–4 (2001); Joyce, E. A., et al., *J Bacteriol*, 182:3638–43 (2000); Lyon, W. R., et al., *Mol Microbiol*, 42:145–57 (2001); and Sperandio, V., et al., *Proc Natl Acad Sci USA*, 96:15196–201 (1999)).

*S. mutans* is a major cariogenic bacterium that normally inhabits a complex, multispecies, biofilm on the tooth surface (dental plaque) (Tanzer, J. M., et al., *J Dent Educ*, 65:1028–37 (2001)). The bacteria produce large amounts of exopolysaccharides, especially in the presence of sucrose, that enable them to adhere to the tooth.

The bacteria also have the ability to produce large amounts of acids from fermentable sugars in the diet. Acid accumulation can eventually dissolve the hard, crystalline structure of the tooth resulting in a carious lesion (Quivey, R. G., et al., *Crit Rev Oral Biol Med*, 12:301–14 (2001)). Previous studies have established some sophisticated interactions among the oral streptococci as well as with other oral bacteria within the same dental plaque (Kolenbrander, P. E., *Enzymol*, 253:385–97 (1995); Kolenbrander, P. E., *Annu Rev Microbiol*, 54:413–37 (2000); and Kolenbrander, P. E., et al., *Infect Immun*, 63:4584–8 (1995)).

There is a need in the art to develop methods and compositions useful for regulating biofilm formation, especially preventing or treating biofilm formation in association with microbial infections.

SUMMARY OF THE INVENTION

The present invention is based on the discovery that interspecies quorum sensing, e.g., LuxS-dependent signal pathway is related to biofilm formation. Accordingly the present invention provides methods for preventing or inhibiting biofilm formation and methods for treating or preventing disease and other conditions associated with biofilm formation. The present invention also provides compositions that are useful for treating microbial infections and infestations associated with biofilm formation.

In one embodiment, the present invention provides a method of preventing or treating the formation of a biofilm on a surface. The method comprises contacting the surface with an agent that increases LuxS-dependent signal pathway in a bacterium or increases an interspecies quorum sensing signal.

In another embodiment, the present invention provides a method of treating or preventing a disease condition associated with a bioflim. The method comprises administering to a subject in need of such treatment an agent, wherein the agent increases LuxS-dependent signal pathway in a bacterium or increases an interspecies quorum sensing signal.

In yet another embodiment, the present invention provides a composition comprising an anti-microbial agent and an agent that increases LuxS-dependent signal pathway in a bacterium or increases an interspecies quorum sensing signal.

In still another embodiment, the present invention provides a method of treating a disease condition associated with bacterial biofilm formation comprising administering to a subject in need of such treatment the composition of the present invention.

In another embodiment, the present invention provides a method of treating a microbial infection associated with biofilm formation. The method comprises administering to a population of bacteria an anti-microbial agent and an agent that increases LuxS-dependent signal pathway in a bacterium or increases interspecies quorum sensing signal.

In yet another embodiment, the present invention provides a method of treating bacterial biofilm formation on a surface. The method comprises contacting the surface with an anti-microbial agent and an agent that increases LuxS-dependent signal pathway in a bacterium or increases interspecies quorum sensing signal.

In another embodiment, the present invention provides a method of preventing or inhibiting bacteria biofilm formation or sensitizing bacteria for an anti-bacteria treatment. The method comprises administering an agent to a population of bacteria, wherein the agent increases LuxS-dependent signal pathway in a bacterium or increases interspecies quorum sensing signal.

SUMMARY OF THE FIGURES

FIG. 1 shows an alignment of the *S. mutans* LuxS protein (SEQ ID NO. 1) and several other representative LuxS proteins. Residues that coordinate a $Zn^{2+}$ ion and comprise the catalytic center of LuxS (H, H, & C) are printed in bold. 1, *V_harveyi* (SEQ ID NO. 2); 2, *S_mutans*; 3, *E_coli* (SEQ ID NO.3); 4, *S_pyogenes* (SEQ ID NO. 4); 5, *B_subtilis* (SEQ ID NO.5).

FIG. 4A illustrates the knockout procedure. Plasmids containing either cloned fragments of *S. mutans* DNA as well as the erythromycin cassette were cut using the indicated restriction sites and then ligated into a linearized pUC19 backbone. The resulting construct was linearized with the unique AatII site and transformed into *S. mutans* for double crossover. FIG. 4B shows that AI-2 production assay confirms that activity was lost in the mutant.

DESCRIPTION OF THE PREFERRED EMBODIMENTS

Figure 2:
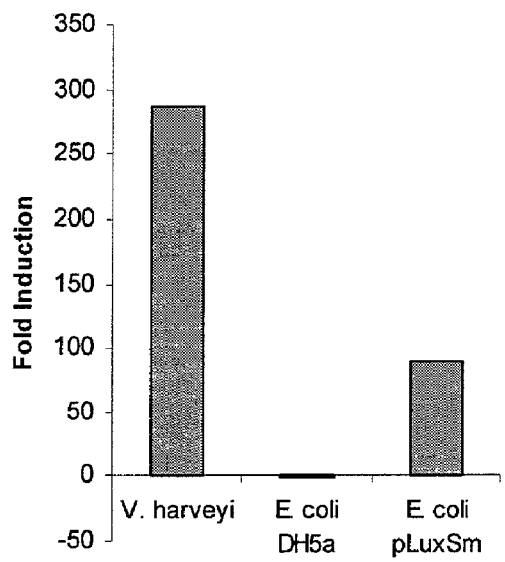
FIG. 2 shows *S. mutans* luxS complements a frameshift mutation in *E. coli* DH5α. *E. coli* DH5α was transformed with an *E. coli-S. mutans* shuttle vector containing an intact copy of the *S. mutans* luxS gene (pLuxSm). This strain was examined for AI-2 production using the luminescence based AI-2 reporter assay. *V. harveyi* strain BB170 (sensor 1⁻, sensor 2⁺) served as a positive control, while *E. coli* DH5α served as a negative control. Luminescence is expressed as fold induction relative to the background values.

The present invention relates in general to the interspecies quorum sensing, LuxS-dependent signal pathway and their association with biofilm formation. It is the discovery of the present invention that increasing interspecies quorum sensing signal or LuxS-dependent signal pathway decreases biofilm formation and increases biofilm's sensitivity to anti-microbial treatment. The present invention provides methods and compositions useful for preventing or treating biofilm formation or microbial infections associated with biofilm formation.

One feature of the present invention provides a method for preventing or treating biofilm formation. According to the present invention, the formation of a biofilm on a surface can be prevented or treated by contacting the surface, e.g., a biological surface or an inanimate or dynamic solid industrial surface such as a heat exchanger or "clean room" surfaces with an agent or administering an agent to a subject, e.g., a human or an animal in need of such treatment, wherein the agent either increases LuxS-dependent signal pathway in a bacterium or increases an interspecies quorum sensing signal. Alternatively, such agent can be administered to a population of bacteria, e.g., more than one bacterium to prevent or decrease the biofilm formation of the bacteria.

According to another feature of the present invention, bacteria, biofilms, or surfaces containing thereof can be sensitized for anti-microbial, e.g. anti-bacteria treatment using the agents of the present invention. For example, the agents of the present invention can be administered to a population of bacteria or bacteria within a biofilm so that these bacteria are primed or sensitized to be less resistant or more susceptible to anti-microbial treatments, e.g., antibiotics, target specific therapeutic agents, detergents, and biocides.

Bacteria or biofilms can be sensitized either prior to or simultaneously with any anti-microbial treatment. For example, the agents of the present invention can be used prior to or in combination with an anti-microbial agent to treat a surface, e.g., industrial or biological surface or subject, e.g., human for biofilm formation or microbial infections such as bacterial infection associated with biofilm formation. The subject in need of such treatment can be any suitable subject, e.g., a human or an animal including a domestic animal such as a horse, dog, or cat.

The agent of the present invention can be any agent known or later discovered that is suitable for the present invention. For example, such agent can be any entity capable of activating the LuxS gene, any expression product of the LuxS gene that is involved in the interspecies quorum sensing, any down stream component in the LuxS-dependent signal pathway including any interspecies quorum sensing signal itself, or any agent capable of increasing the function or activity of an interspecies quorum sensing signal.

In one embodiment, an agent that increases LuxS-dependent signal pathway is LuxS protein which includes full-length LuxS protein and one or more partial LuxS proteins having substantially the same function of the full-length LuxS protein in synthesizing interspecies quorum sensing signal, e.g., autoinducer-2 in a bacterium. In another embodiment, an agent that increases an interspecies quorum sensing signal is autoinducer-2 which includes autoinducer-2 and an analog or derivative thereof functioning as an interspecies quorum sensing signal or having the same or similar function of autoinducer-2 in interspecies quorum sensing. For example, WO 01/85664 discloses various autoinducer-2 analogs which could be suitable for the present invention.

The methods provided by the present invention can be used to prevent or treat any biofilm. Biofilms in general are coatings formed via bacteria adhering to a surface, e.g., solid surface. Usually a population of bacteria interact or signal with each other directly or indirectly to form a highly hydrated matrix of exopolymers, typically polysaccharide, and other biopolymers on a surface. The formation of biofilm could take several steps and usually includes initial attachment and full maturity into a stable community.

According to the present invention, biofilms prevented or treated by the present invention can contain single species or multiple species bacteria. In one embodiment, the biofilms are associated with microbial infection or a disease condition including, without limitation, dental caries, periodontal disease, prostatitis, osteomyelitis, septic arthritis, and cystic fibrosis. In another embodiment, the biofilms contain Gram positive bacteria including without limitation Streptococcus, e.g. *S mutans*. In yet another embodiment, the extracellular matrix or exopolymers of the biofilms is regulated by or responsive to LuxS-dependent interspecies quorum sensing.

In still another embodiment, the biofilms are associated with a surface, e.g., a solid surface. Such surface can be the surface of any industrial structure, e.g., pipeline or the surface of any structure in animals or humans. For example, such surface can be any epithelial surface, mucosal surface, or any host surface associated with bacterial infection, e.g., persistent and chronic bacterial infections. The surface can also include any surface of a bio-device in animals or humans, including without limitation, bio-implants such as bone prostheses, heart valves, and pacemakers.

In addition to surfaces associated with biofilm formation in a biological environment, the surfaces treated by the present invention can also be any surface associated with industrial biofilm formation. For example, the surfaces being treated can be any surface associated with biofouling of pipelines, heat exchangers, air filtering devices, or contamination of computer chips or water-lines in surgical units like those associated with dental hand-pieces.

According to yet another feature of the present invention, it provides compositions useful for treating biofilm formation and infections associated with biofilm formation. The composition of the present invention contains an anti-microbial entity and an agent of the present invention. The anti-microbial entity can be any that is suitable for the present invention, e.g., detergents, biocides, antibiotics or target specific therapeutic entities. The antibiotics include, without limitation, penicillin, quinoline, vancomycin, sulfonamide, ampicillin, ciprofloxacin, and sulfisoxazole. The target specific therapeutic entities can include a targeting moiety coupled to an anti-micorbial peptide moiety. U.S. application Ser. No. 10/077,624 discloses various target specific anti-microbial entities and is incorporated herein by reference.

The composition or agent of the present invention can also include one or more other non-active ingredients, e.g., ingredients that do not interfere with the function of the active ingredients. For example, the composition or agent of the present invention can include a suitable carrier or be combined with other therapeutic agents.

A suitable carrier can be a powder, encapsulated solid, or an aqueous carrier including any safe and effective materials for use in the compositions of the present invention. In one embodiment, an aqueous carrier is used for the compositions of the present invention in oral formations and includes, without limitation, thickening materials, humectants, water, buffering agents, abrasive polishing materials, surfactants, titanium dioxide, flavor system, sweetening agents, coloring agents, and mixtures thereof.

A suitable carrier can also be a pharmaceutically acceptable carrier that is well known to those in the art. Such carriers include, without limitation, large, slowly metabolized macromolecules, e.g., proteins, polysaccharides, polylactic acids, polyglycolic acids, polymeric amino acids, amino acid copolymers, and inactive virus particles.

Pharmaceutically acceptable salts can also be used in the composition, for example, mineral salts such as sodium or stannous fluorides, or sulfates, as well as the salts of organic acids such as acetates, proprionates, carbonates, malonates, or benzoates. The composition can also contain liquids, e.g., water, saline, glycerol, and ethanol, as well as substances, e.g., wetting agents, emulsifying agents, or pH buffering agents.

According to another feature of the present invention, the compositions or agents of the present invention can be used to treat or prevent disease conditions associated with biofilm formation. For example, an effective amount of the composition or agent of the present invention can be administered to a subject, e.g., a human or an animal to treat or prevent disease conditions associated with biofilm formation. Alternatively, the agent of the present invention and an anti-microbial agent can be administered as separate compositions, either sequential or simultaneously to a subject to treat or prevent disease conditions associated with biofilm formation. Various disease conditions are associated with biofilm formation including, without limitation, dental caries, periodontal disease, prostatitis, osteomyelitis, septic arthritis, cystic fibrosis, and heart valve vegetations. In one embodiment, the disease conditions are on an epithelial surface or a mucosal surface, e.g., mouth, vagina, gastrointestinal tract, and esophageal tract.

In generally, an effective amount of the agent or composition of the present invention to be administered to a subject can be determined on a case-by-case basis. Factors to be considered usually include the total surface area to be treated, age, body weight, stage of the condition, other disease conditions, duration of the treatment, and the response to the initial treatment.

Typically, the agents or compositions used in the present invention are prepared as a topical or an injectable, either as a liquid solution or suspension. However, solid forms suitable for solution in, or suspension in, liquid vehicles prior to injection can also be prepared. The composition can also be formulated into an enteric-coated tablet or gel capsule according to known methods in the art. In one embodiment, the composition of the present invention can be formulated onto the surfaces of industrial or biological structures or as coatings thereto, e.g., coatings to prosthetic heart valves, prosthetic hearts, vascular stents, or prosthetic joints.

The agents or compositions of the present invention may be administered in any way which is industrially or medically acceptable which may depend on the condition or injury being treated. Possible administration routes include injections, by parenteral routes such as intravascular, intravenous, intraepidural or others, as well as oral, nasal, ophthalmic, rectal, vaginal, topical, or pulmonary, e.g., by inhalation. The compositions may also be directly applied to industrial or tissue surfaces. Sustained release, pH dependent release, or other specific chemical or environmental condition mediated release administration is also specifically included in the invention, by such means as depot injections or erodible implants.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

In this study, we demonstrate that luxS dependent quorum sensing is involved in biofilm formation of *Streptococcus mutans*. *S. mutans* is a major cariogenic bacterium in the multi-species bacterial biofilm commonly known as dental plaque. An ortholog of luxS in *S. mutans* was identified using the data available in the *S. mutans* genome project (http://www.genome.ou.edu/smutans.html). Using an assay developed for the detection of the LuxS-associated quorum sensing signal Autoinducer 2 (AI-2), it was demonstrated that this ortholog was able to complement the luxS negative phenotype of *E. coli* DH5α. It was also shown that AI-2 is indeed produced by *S. mutans*. AI-2 production is maximal during mid to late-log growth in batch culture.

Mutant strains devoid of the luxS gene were constructed and found to be defective in producing AI-2 signal. There are also marked phenotypic differences between wildtype and the luxS mutants. Microscopic analysis of in vitro grown biofilm structure revealed that the luxS mutant biofilms adopted a much more granular appearance, rather than the relatively smooth, confluent layer normally seen in wild type. These results demonstrate that LuxS-dependent signal play an important role in biofilm formation of *S. mutans*.

EXAMPLE 1

Material and Methods

Bacterial Strains and Culture Conditions

All bacterial strains used in this study and their characteristics are listed in Table 1. All *S. mutans* strains were grown in brain heart infusion media (Difco) or on brain heart infusion agar plates. luxS deletion mutants were grown using the same media supplemented with 15 μg/mL erythromycin. All *S. mutans* strains were grown anaerobically at 37° C. *E. coli* cells were grown in Luria-Bertani (LB) medium with aeration at 37° C. *E. coli* cells carrying plasmids were grown in LB medium containing 100 μg/mL erythromycin. *V. harveyi* BB170 (sensor 1⁻, sensor 2⁺) was kindly provided by B. Bassler (Princeton University) and grown in AB medium (37) overnight at 30° C.

TABLE 1

Bacterial strains used in this study

| Strain | Relevant Characteristics | Reference |
| --- | --- | --- |
| *S. mutans* 25175 | WT Em$^s$ | ATCC |
| *S. mutans* GS-5 | WT Em$^s$ | (16) |
| JM03 | ΔluxS Em$^r$ in 25175 background | This work |
| JM01 | ΔluxS Em$^r$ in GS-5 background | This work |
| *E. coli* DH5α | supE44 ΔlacU169 (Φ80lacZΔM15)hsdR17 recA1 endA1 gyrA96 thi-1 relA1 | (17) |
| *E. coli* XL1 Blue | recA1 endA1 gyrA96 thi-1 hsdR17 supE44 relA1 lac [F' proAB lacI$^q$ZDM15 Tn10(Tet$^r$)] | (3) |

Cloning and Analyses of the *S. mutans* LuxS Gene

A 990-bp DNA fragment containing the luxS gene from *S. mutans* strain 25175 was PCR amplified from genomic DNA using the primers WTlux5 (5'-GATGCTGCACGCTCTGTC-3') (SEQ ID NO. 6) and WTlux3 (5'-GCAGTTAGGGTATC-CATCC-3') (SEQ ID NO. 7). Primer sequences were designed using sequence data obtained from the *S. mutans* Genome Sequencing Project, University of Oklahoma (B. A. Roe, R. Y. Tian, H. G. Jia, Y. D. Qian, S. P. Lin, S. Li, S. Kenton, H. Lai, J. D. White, R. E. McLaughlin, M. McShan, D. Ajdic and J. Ferretti. http://www.genome.ou.edu/smutans.html). The resulting fragment was cloned into the TOPO TA cloning vector (Invitrogen) and sequenced.

RNA Isolation and RT-PCR

*S. mutans* total RNA was isolated as follows. 25 mL cultures were grown overnight as previously described. Cells were centrifuged and resuspended in 1.5 mL of TE buffer and then lysed using a Mini-Bead Beater 8 according to manufacturer's instructions. 150 μL of lysate was then passed through a Qiashredder column (Qiagen) and 100 μL of the resulting lysate was used for total RNA isolation with the RNeasy mini kit (Qiagen). cDNA buffer was added to RNA samples to obtain a 1× solution and 3 μL of RQ1 RNase free DNase was added to the sample and incubated overnight at 37° C. Reverse Transcription was performed according to manufacturer's protocol using random hexamers.

AI-2 Assay

The AI-2 luminescence reporter assay was performed essentially as described (38), with the following modifications. To obtain cell free conditioned media, *S. mutans* was grown overnight as described. Stationary phase cells were resuspended in AB media to an $OD_{600}$ of 0.4. Cells were then incubated at 37° C. with aeration for 3 hrs. After the incubation period, cells were pelleted by centrifugation, and the resulting supernatant was filtered through a 0.22 mm pore sized filter (Millipore). The cell free conditioned media was either used immediately or stored at −20° C.

To determine luminescence, an overnight culture of *V. harveyi* BB170 was diluted 1:1000 into fresh AB medium and 180 μL of cells was added to each 1.5 mL microfuge tube. Conditioned media (20 μL) was then added to the cells at a 10% (vol/vol) final concentration. Positive control samples were obtained by adding cell free conditioned media from an overnight culture of *V. harveyi* BB170 to a final concentration of 10%. In some cases, conditioned media from a wildtype culture of *S. mutans* served as an additional positive control.

To determine levels of background luminescence, a sample containing 200 μL of 1:1000 diluted *V. harveyi* was also included. In some cases, *E. coli* DH5α served as a negative control. All samples were measured hourly until peak induction at the 3 hr time point. Measurements were collected using a TD 20/20 luminometer and expressed as arbitrary luminescence units.

Construction and Analyses of *S. mutans* LuxS Mutants 2 (1 Kb) fragments containing regions of DNA immediately upstream and downstream of the luxS translational start and stop codons respectively were amplified from genomic DNA template using the primers 2×upF (5'-GCGGATCCT-CAAGCTCTCAAGCGTTCGG-3') (SEQ ID NO. 8) and 2×upR (5'-CGAGATCTATAAGACGGACATAAGGGGC-3') (SEQ ID NO. 9) as well as 2×downF (5'-GCCTCGAG-CAGATGATCCTTTTGAGCGTC-3') (SEQ ID NO. 10) and 2×downR (5'-CGTCTAGACGGATGCAAAGAGAAC-GAAG-3') (SEQ ID NO. 11). Primer sequences were designed using sequence data obtained from the S. mutans Genome Sequencing Project, University of Oklahoma (http://www.genome.ou.edu/smutans.html). The resulting fragments were cloned into the TOPO TA cloning vector (Invitrogen).

To obtain the necessary fragments, four separate restriction digests were constructed: the upstream fragment was cut from the vector using BamHI and BglII, the downstream fragment was cut from the vector using XhoI and XbaI, the erythromycin cassette was cut from the plasmid pJT10 (unpublished plasmid by J. P Tsai and W. Shi) using BglII and XhoI, and the pUC19 vector was cut with BamHI and XbaI. The resulting fragments were all gel purified (Qiagen), precipitated, and added to one mass ligation reaction. The resulting construct was then checked by restriction analysis and PCR for the proper configuration of the knockout vector (pUCluxKO).

Next, the plasmid was linearized with the unique cutting enzyme AatII and transformed into S. mutans. Transformants were selected for resistance to 15 μg/mL erythromycin. Confirmation of DNA integration was performed by PCR using primers IntluxF (5'-AAGAGTTTGGACCTAAAGGC-3') (SEQ ID NO. 12), IntluxR (5'-CCCACAGGACTCAAT-AGTTG-3') (SEQ ID NO. 13), UpluxF (5'-CTCGACGAAT-AGGATCAAAGC-3') (SEQ ID NO. 14), DownluxR (5'-GAGCCATCACACAGCAAAAAC-3') (SEQ ID NO. 15), ermA (5'-AGTGTGTTGATAGTGCAGTATC-3') (SEQ ID NO. 16), and ermM (5'-GAAGCTGTCAGTAGTATACC-3') (SEQ ID NO. 17). All mutants confirmed by PCR were further analyzed for their ability to produce AI-2 using the methods described above.

Growth of In Vitro Biofilm

Biofilms of S. mutans were grown as follows. Individual sterile culture dishes were filled with 2.5 mL of brain heart infusion broth supplemented with 1% (w/v) sucrose. Next, a sterile 18 mm glass microscope cover slip was added to each dish and the culture dish was covered. Each sample was then inoculated with a defined volume of overnight culture. The dishes were incubated anaerobically at 37° C. overnight.

Microscopic Analyses of In Vitro Grown Biofilm

Glass cover slips containing attached biofilm were removed from overnight cultures and rinsed briefly with water. These could be directly viewed using phase contrast and darkfield microscopy. For fluorescently labeled samples, the biofilms were first removed from the culture dish and placed into another dry culture dish. Next, 20 μL of anti-S. mutans mouse monoclonal antibody solution (SWLA1) was added to the attached biofilm in each culture dish and incubated at room temperature for 30 minutes (Shi, W., et al., Hybridoma, 17:365–71 (1998)).

After the incubation period, 5 μL of 2° antibody (FITC conjugated goat anti-mouse) was added to the biofilms and incubated at room temperature for an additional 10 minutes. Finally, the cover slip was briefly rinsed with water to remove excess antibodies and unattached cells and the sample was immediately imaged using fluorescence microscopy.

Treatment of In Vitro Biofilm with SDS and Antibiotics

Biofilms were grown overnight using previously described conditions. For treatment with SDS, cover-slips were removed from overnight incubation and rinsed briefly. These were then placed into a fresh culture dish and 2mL of sterile, 1% (w/v) SDS solution was added to each dish. The biofilms were placed on a standard shaker set at 150 rpm for one hour at room temperature. Next, supernatant samples were checked at 40× magnification to confirm that cells were fully individualized and not connected in chains. These samples were measured for their $OD_{600}$ values. For treatment with antibiotics, biofilms were again grown under standard conditions overnight. The following day, the spent media was changed and replaced with BHI supplemented with 1% (w/v) sucrose solution. Ampicillin was added at either 50 μL or 500 μg/mL. These biofilms were allowed to grow overnight under anaerobic conditions at 37° C. The following day, biofilms were removed from incubation and sonicated until the cells were fully dispersed. A $10^6$ fold dilution of each sample was plated on non-selective BHI agar plates and incubated anaerobically overnight at 37° C.

EXAMPLE 2

Identification and Isolation of S. mutans luxS Gene

To determine whether S. mutans may posses an interspecies quorum system, it was first necessary to identify a candidate ortholog of luxS, the enzyme required for AI-2 production. Using the luxS gene from Vibrio harveyi, we performed a BLAST search of the University of Oklahoma Streptococcus mutans Genome Sequence Database. A candidate open reading frame was identified.

The ORF appears to be an isolated gene (no other convincing ORF's nearby) and encodes a protein of 160 amino acids, which is similar in size to other reported LuxS proteins. It is homologous to the V. harveyi LuxS protein with 38% amino acid identity and 57% similarity.

Using this sequence data, primers were designed to amplify a region about 500 bp upstream of the translation start site and about 100 bp downstream of the translational stop site. This fragment was PCR amplified, cloned into the TOPO TA cloning vector, and sequenced to confirm the identity of the gene. After the fragment was confirmed to be the same ORF identified in the Sequence Database, an NCBI PSI BLAST search of the candidate gene was conducted.

The results yielded strong homologies to numerous LuxS proteins from other Gram positive and Gram negative bacteria. The strongest homologies (identity/similarity) were to other Gram positive species such as Streptococcus pyogenes (84%/92%), Streptococcus pneumoniae (83%/91%), Lactococcus lactis (64%/79%), and Clostridium perfringens (45%/64%), but there were also significant homologies to Gram negative species such as Neisseria meningitidis (36%/58%), Escherichia coil (37%/59%), and Haemophilus influenzae (37%/58%). A multiple alignment of the putative S. mutans LuxS protein and those from V. harveyi, E. coli, S. pyogenes, and B. subtilis demonstrated a high degree of similarity (FIG. 1).

Of greatest interest was the location of several highly conserved amino acids (H, H, & C), which are reported to coordinate a $Zn^{+2}$ ion and form the catalytic center of the protein (19). These amino acids and several others that are reportedly invariant are all conserved in the S. mutans LuxS protein (FIG. 1).

EXAMPLE 3

Complementation of an E. coli luxS Mutant with S. mutans luxS Gene

After confirming the identity of the candidate ORF, it was necessary to determine whether this gene also had the characteristic AI-2 synthase activity. This was accomplished by complementing an AI-2 production defect in E. coli DH5α. This strain of E. coli is known to have a frameshift mutation in its luxS gene. Therefore, a plasmid containing the luxS gene and some upstream sequence was transformed into DH5α and AI-2 activity was measured using the reporter assay described by Surrette et al (Surette, M. G., et al., *Proc Natl Acad Sci USA*, 95:7046–50 (1998)).

As shown in FIG. 2, our assay confirmed that E. coli DH5α was AI-2 negative and also demonstrated that the presence of the luxS containing plasmid was sufficient to induce luminescence 89-fold over background.

EXAMPLE 4

Secretion of an AI-2-like Signal by S. mutans

To determine whether S. mutans had endogenous AI-2 activity, we again employed the AI-2 reporter assay. Initial screens using this assay failed to demonstrate any convincing AI-2 activity. These first experiments were all performed as had been described in previous reports. Cells were grown to various $OD_{600}$ values using standard growth media and the resulting conditioned media was used as a source of AI-2 molecules. However, these experiments consistently yielded background levels of luminescence.

Figure 3:
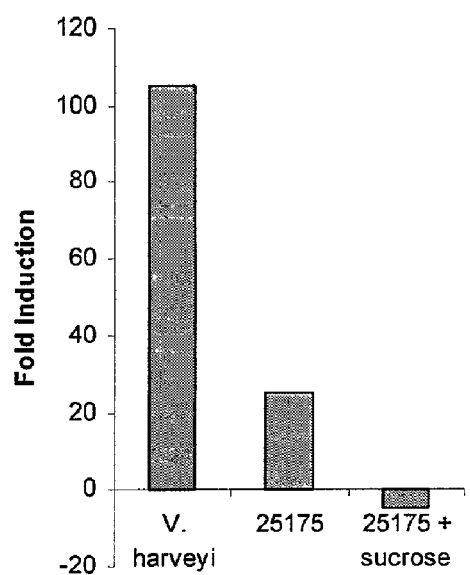
FIG. 3 shows AI-2 induction in the presence or absence of sugar. *S. mutans* was grown and assayed as described in Materials and Methods. Cells were grown overnight and resuspended to an $OD_{600}$ of 0.4 in reporter assay (AB) media and incubated with aeration for 3 hours at 37° C. One sample was incubated in AB alone, while the other had sucrose added to a final concentration of 1%. The presence of sucrose in the media caused a potent reduction in luminescence to below background values.

In E. coli, it had been demonstrated that the presence of glucose in the growth media caused a strong induction of AI-2 (Surette, M. G., et al., *Proc Natl Acad Sci USA*, 95:7046–50 (1998)). Therefore, we decided to try adding glucose as well as sucrose (S. mutans preferred carbon source) to the growth media in an effort to demonstrate AI-2 production. Since S. mutans is an acidogenic bacterium, pH readings were taken to ensure that there were no negative effects due to lowered pH. Interestingly, these experiments consistently yielded lower than background levels of luminescence (FIG. 3).

In an effort to circumvent this problem, we decided to resuspend overnight cultures in the AI-2 assay media at various $OD_{600}$ ranges. This media only allows for very limited growth of S. mutans, but is able to keep the cells alive long enough for the production of AI-2 signal molecules. After assaying samples produced in this manner, it was immediately possible to measure induced luminescence. Samples assayed at mid to late log growth phase had the strongest induction over background, while the induction tended to drop at stationary phase. Mid to late log samples typically produced about 25-fold induction of the reporter strain (*V. harveyi*) luciferase operon expression over background levels (FIG. 3). As a further confirmation, luxS was shown to be expressed in S. mutans via RT-PCR.

EXAMPLE 5

Construction of S. mutans luxS Mutants

Figure 4A:
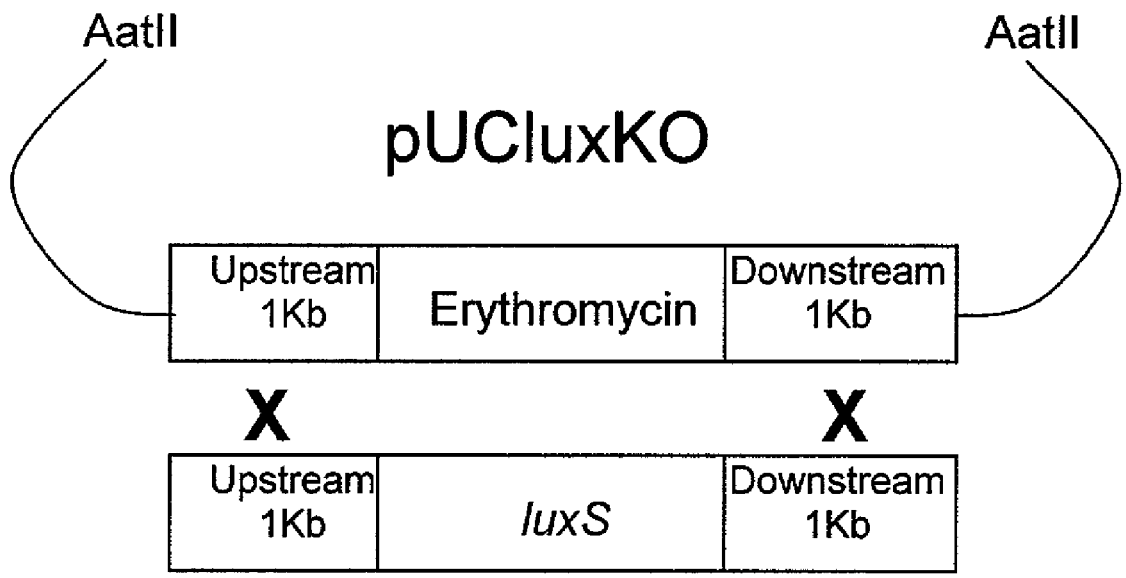
FIGS. 4A and 4B show luxS knockout in *S. mutans*.
Figure 4B:
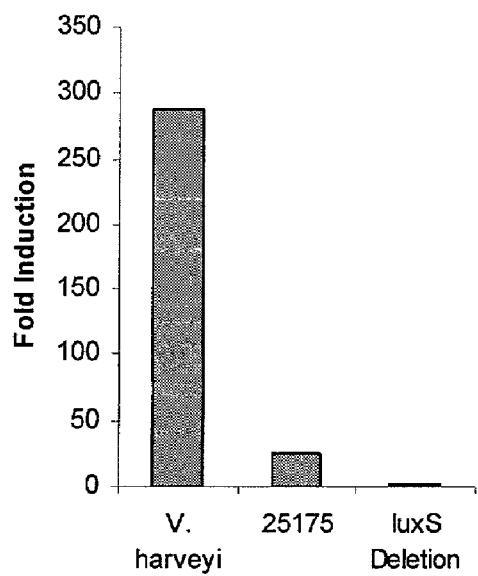

After confirming that this ORF was a functional luxS gene and that it was involved in the production of AI-2 signal molecules, we decided to disrupt the function of this gene by allelic replacement to check for any resulting phenotypic changes. luxS was deleted using a double crossover construct as illustrated in FIG. 4A and described in Example 1. The double crossover event was confirmed by various PCR reactions. As a further confirmation of the construct, we tested these mutants for the loss of AI-2 activity. As shown in FIG. 4B, wildtype S. mutans had a luminescence induction of about 25 fold, while the mutant retained essentially background levels of luminescence.

EXAMPLE 6

General Phenotypic Characterization of S. mutans luxS Mutants

After confirmation of the deletion of luxS and subsequent loss of AI-2 activity, the next step was to quantify any resulting physiological changes in the luxS mutant. When the mutant colonies were plated, there were no obvious phenotypic differences in colony morphology. In batch culture there was no obvious difference in growth rate, nutrient requirements, or acid production.

EXAMPLE 7

Altered Bioflim Structure of the S. mutans luxS Mutants

Our next investigation of mutant phenotypes was to determine if there were any alterations of biofilm structure as a result of loss of AI-2 production. Both wild-type and mutant cells were able to form a biofilm when grown on a solid surface overnight.

Upon visual inspection, there was a noticeable difference in biofilm structure from the wild-type. Without the aid of magnification, wild-type biofilm generally has a very confluent appearance with no major discernable features. In contrast, the luxS mutant biofilm had a very rough texture. Under 20× and 40× magnification, this difference is even more apparent. Wild-type biofilms are very uniform with complete coverage of the attached surface. They also tend to have relatively small aggregates spread fairly evenly throughout the biofilm matrix. luxS mutant biofilms are quite different. Their organization seems much more heterogeneous. There were noticeable large gaps in the biofilm matrix and the cell aggregates appeared much larger. Using fluorescence imaging, there is a clear indication that the sizes of mutant aggregates tended to be much larger than those of wild-type.

Figure 5:
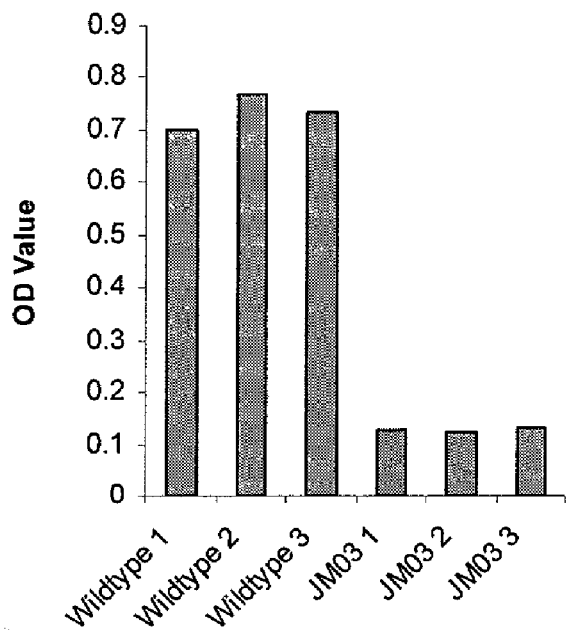
FIG. 5 shows the results of biofilms tested for their ability to resist detergent treatment with SDS. Three samples of wildtype and mutant biofilms grown on glass coverslips were shaken at 150 rpm for one hour. The $OD_{600}$ of the resulting supernatants were compared.

As biofilms are known to be very resistant to detergents and biocides, we were also interested to determine if this property was influenced by the luxS mutation. Overnight biofilms of wildtype and the luxS mutant were incubated in a 1% solution of SDS and shaken at 150 rpm for one hour. These supernatants were then checked by microscopy to ensure that cells were not clumped, and subsequently, measured for the $OD_{600}$. It was found that the wildtype supernatants had an $OD_{600}$ value that averaged about 6 fold greater than that of the mutant (FIG. 5B), which suggested that luxS mutant biofilms were more resistant to detergent treatment. We also treated biofilms of wildtype and the luxS mutant with the antibiotic ampicillin at 50 μg/mL or 500 μg/mL for 16 hours. We found that very few (<1%), if any, wildtype cells survived treatment with 50 μg/mL ampicillin and that none survived the treatment with 500 μg/mL. In contrast, numerous cells (>10%) within the luxS mutant biofilms survived the treatment with 50 μg/mL ampicillin and even with 500 μg/mL ampicillin.

Within the past couple of years, there has been a plethora of data describing various physiological functions from both Gram positive and Gram negative species which are subject to regulation by luxS (Chung, W. O., et al., *J Bacteriol*, 183: 3903–9 (2001); Day, W. A., Jr., et al., *Infect Immun*, 69:15–23 (2001); Fong, K. P., et al., *Infect Immun*, 69:7625–34 (2001); Lyon, W. R., et al., *Mol Microbiol*, 42:145–57 (2001); and Sperandio, V., et al., *Proc Natl Acad Sci USA*, 96:15196–201 (1999)). Much of the reported data has supported the hypothesis that luxS is somehow involved in regulating virulence factor expression. Furthermore, there has not been a reported scenario in which mutating this gene has lead to severe growth impairment, which suggests that the production of AI-2 is not a requirement for basic metabolic processes.

Our current findings are consistent with these same trends. After deletion of the luxS gene, there were no noticeable changes in growth patterns or basic nutrient requirements. However, *S. mutans* is a predominantly biofilm dwelling organism and as such depends on its biofilm production for virulence in the oral cavity. The involvement of luxS in the proper development of *S. mutans* biofilms also yields some insight into the role of interspecies communication in multispecies biofilm formation. *S. mutans* normally grows amongst hundreds of other competing species of oral bacteria and must therefore employ strategies to survey and respond to other species that compete for control of available ecological niches in the mouth.

One possible strategy to accomplish this goal would be through the use of luxS based interspecies signaling. We believe that as an early colonizer of the tooth surface, AI-2 signal molecules is an important factor in regulating biofilm related gene expression to help modulate energy utilization for growth in an extremely competitive environment.

Through a search of the *S. mutans* genome database, we were able to find a candidate luxS ortholog. Despite having a gene whose encoded protein aligned exceedingly well with other known LuxS proteins, initial attempts to demonstrate the production of AI-2 molecules all seemed to suggest that they were not produced. Indeed, there are reports of other luxS containing bacteria that have not been shown to induce the AI-2 reporter assay (Frias, J., et al., *Infect Immun*, 69:3431–4 (2001) and Surette, M. G., et al., *Proc Natl Acad Sci USA*, 96:1639–44 (1999)). It was especially perplexing to find that the presence of glucose and sucrose in the growth media caused the AI-2 reporter assay to yield values below background levels, while glucose was known to cause a potent induction of AI-2 activity in *E. coli*.

Part of the answer came from the media itself. It seems that detectable AI-2 activity drops in rich media and is potently inhibited in the presence of glucose and to an even greater extent with sucrose. This phenomenon may explain why a recent screen for AI-2 activity in various oral pathogens failed to demonstrate AI-2 activity in *S. mutans* strain 25175 (Frias, J., et al., *Infect Immun*, 69:3431–4 (2001)).

There also exists the possibility that AI-2 is still produced in rich media and/or in the presence of sugar, but the reporter assay is inhibited by some factor(s) secreted by *S. mutans* when grown under these conditions. Indeed, *S. mutans* is known to produce a battery of various inhibitory molecules such as lantibiotics and non-lantibiotic bacteriocins (Chen, P., et al., *Appl Enviro Microbiol*, 65:1356–60 (1999); Qi, F., et al., *Appl Environ Microbiol*, 67:15–21 (2001); and Qi, F., et al., *Appl Environ Microbiol*, 65:3880–7 (1999)). In addition, it is also known that in the presence of sugars, *S. mutans* has a distinct growth advantage over other competing oral bacteria. Therefore, it is possible that sugar stimulates *S. mutans* to produce an inhibitor that affected either luciferase production in the AI-2 assay or perhaps even an inhibitor that acted at level of the AI-2 signaling process. Even though an AI-2 related inhibitory signal in *S. mutans* is currently unknown, its production could give additional explanations for *S. mutans* ability to gain a growth advantage over competitors within its multispecies biofilm.

Our data show that both wild-type and the luxS mutant of *S. mutans* are able to form biofilms on solid surfaces. This is consistent with previous reports (Wen, Z. T., et al., *Appl Environ Microbiol*, 68:1196–203 (2002)). Our investigation demonstrates that the luxS mutant has several altered biofilm phenotypes: increased size of cell aggregates, altered biofilm structure, and an increased biofilm resistance to detergents and antibiotics. These phenotypes reveal that luxS has a regulatory role on one or more genes related to biofilm formation. In *S. mutans*, EPS consists of insoluble glucans, which are primarily synthesized by the activity of the GtfB enzyme. Glucans make the cells more generally adherent in a nonspecific manner, but are also known to interact with glucan binding proteins for specific interactions (Hazlett, K. R., et al., *Infect Immun*, 67:3909–14 (1999) and Mattos-Graner, R. O., et al., *Infect Immun*, 69:6931–41 (2001)). Therefore, the observed phenotypes can be partially due to a greater production of glucan, an increase in specific receptors for glucan or other cell wall components, or possibly a combination of both factors. These questions are currently being addressed using a proteomics approach.

In summary, we have identified a luxS ortholog in *S. mutans* and demonstrated a corresponding AI-2 activity in the AI-2 assay. When luxS was inactivated, AI-2 activity was abolished with concomitant changes in biofilm structure and resistance to detergents and antibiotics. Taken together, this study provides evidence for the involvement of LuxS in bacterial biofilm formation. It also demonstrates that AI-2 molecules or its analogs could be used to alter biofilm structure in *S. mutans* and/or make the bacteria within its biofilm more accessible to detergent and/or antibiotic treatments.

Although the invention has been described with reference to the presently preferred embodiment, it should be understood that various modifications can be made without departing from the spirit of the invention. Accordingly, the invention is limited only by the following claims.

What is claimed is:

1. A method of inhibiting or treating the formation of a biofilm comprising S. mutans on a surface, said method comprising contacting the surface with autoinducer-2 in an amount effective to increase Lux-S dependent signal pathway in a bacterium.

2. The method of claim 1, wherein the biofilm further comprises other Gram positive bacteria.

3. The method of claim 1, wherein the biofilm comprises more than one species of bacteria.

4. The method of claim 1, wherein the biofilm further comprises Streptococcus sp. other than S. mutans.

5. The method of claim 1, wherein the extracellular matrix of the biofilm is regulated by LuxS-dependent signal pathway.

6. The method of claim 1, wherein the surface is a solid surface.

7. The method of claim 1, wherein the surface is an epithelial or mucosal surface of a mammal.

8. The method of claim 1, wherein the surface is associated with bacterial infection.

9. A method of inhibiting or treating the formation of a biofilm comprising S. mutans on a surface, said method comprising contacting the surface with autoinducer-2 in an amount effective to increase an interspecies quorum sensing signal.

10. A method of treating a condition associated with formation of a biofilm comprising S. mutans, said method comprising administering to a subject in need of such treatment autoinducer-2 in an amount effective to increase LuxS-dependent signal pathway in a bacterium.

11. The method of claim 10, wherein the biofilm further comprises other Gram positive bacteria.

12. The method of claim 10, wherein the biofilm comprises more than one species of bacteria.

13. The method of claim 10, wherein the biofilm further comprises Streptococcus sp. other than S. mutans.

14. The method of claim 10, wherein the extracellular matrix of the biofilm is regulated by LuxS-dependent signal pathway.

15. A method of treating a condition associated with formation of a biofilm comprising S. mutans, said method comprising administering to a subject in need of such treatment autoinducer-2 in an amount effective to increase an interspecies quorum sensing signal.

16. A method of treating a condition associated with formation of a biofilm comprising S. mutans, said method comprising administering to a subject in need of such treatment a composition comprising an anti-microbial agent and autoinducer-2 in an amount effective to increase LuxS-dependent signal pathway in a bacterium.

17. The method of claim 16, wherein the condition is on an epithelial or a mucosal surface.

18. The method of claim 17, wherein the mucosal surface is selected from the group consisting of mouth, vagina, gastrointestinal tract, and esophageal tract.

19. The method of claim 16, wherein the condition is an oral infection.

20. The method of claim 16, wherein the condition is caused by S. mutans.

21. A method of treating a condition associated with formation of a biofilm comprising S. mutans, said method comprising administering to a subject in need of such treatment a composition comprising an anti-microbial agent and autoinducer-2 in an amount effective to increase an interspecies quorum sensing signal.

22. A method of treating a microbial infection associated with formation of a biofilm comprising S. mutans, said method comprising administering to a population of bacteria an anti-microbial agent and autoinducer-2 in an amount effective to increase LuxS-dependent signal pathway in a bacterium.

23. A method of treating microbial infection associated with formation of a biofilm comprising S. mutans, said method comprising administering to a population of bacteria an anti-microbial agent and autoinducer-2 in an amount effective to increase interspecies quorum sensing signal.

24. A method of treating formation of a biofilm comprising S. mutans on a surface comprising contacting the surface, said method with an anti-microbial agent and autoinducer-2 in an amount effective to increase LuxS-dependent signal pathway in a bacterium.

25. A method of treating formation of a biofilm comprising S. mutans on a surface comprising contacting the surface, said method with an anti-microbial agent and autoinducer-2 in an amount effective to increase interspecies quorum sensing signal.

26. A method of sensitizing bacteria for an anti-bacteria treatment comprising administering to a biofilm population of bacteria comprising S. mutans an amount of autoinducer-2 effective to increase LuxS-dependent signal pathway in a bacterium.

27. A method of sensitizing bacteria for an anti-bacteria treatment comprising administering to a biofilm population of bacteria comprising S. mutans an amount of autoinducer-2 effective to increase, interspecies quorum sensing signal.

* * * * *

UNITED STATES PATENT AND TRADEMARK OFFICE
CERTIFICATE OF CORRECTION

| | | |
|---|---|---|
| PATENT NO. | : 7,427,408 B2 | Page 1 of 1 |
| APPLICATION NO. | : 10/164446 | |
| DATED | : September 23, 2008 | |
| INVENTOR(S) | : Justin Merritt et al. | |

It is certified that error appears in the above-identified patent and that said Letters Patent is hereby corrected as shown below:

In the specification:

Column 1, Line 3, please insert --STATEMENT AS TO RIGHTS TO INVENTIONS MADE UNDER FEDERALLY SPONSORED RESEARCH AND DEVELOPMENT--

Insert into the next line right below the above statement --This invention was made with Government support of Grant No. AI009268 awarded by the National Institutes of Health. The Government has certain rights in this invention.--

Signed and Sealed this

Twenty-seventh Day of October, 2009

David J. Kappos
*Director of the United States Patent and Trademark Office*